(12) United States Patent
Fujita et al.

(10) Patent No.: US 9,285,346 B2
(45) Date of Patent: Mar. 15, 2016

(54) PIPE PROCESSING DEVICE AND PIPE PROCESSING METHOD

(75) Inventors: Jun Fujita, Tokyo (JP); Kyoichi Yoshioka, Tokyo (JP); Yoshikatsu Takeda, Tokyo (JP)

(73) Assignee: MITSUBISHI HEAVY INDUSTRIES, LTD., Tokyo (JP)

( * ) Notice: Subject to any disclaimer, the term of this patent is extended or adjusted under 35 U.S.C. 154(b) by 352 days.

(21) Appl. No.: 13/990,477

(22) PCT Filed: Feb. 21, 2012

(86) PCT No.: PCT/JP2012/054133
§ 371 (c)(1),
(2), (4) Date: May 30, 2013

(87) PCT Pub. No.: WO2012/137551
PCT Pub. Date: Oct. 11, 2012

(65) Prior Publication Data
US 2013/0239688 A1    Sep. 19, 2013

(30) Foreign Application Priority Data

Apr. 4, 2011    (JP) .................................. 2011-083116

(51) Int. Cl.
*G01N 29/04*    (2006.01)
*G01N 29/24*    (2006.01)
(Continued)

(52) U.S. Cl.
CPC .............. *G01N 29/04* (2013.01); *F22B 37/003* (2013.01); *G01B 17/00* (2013.01); *G01N 29/043* (2013.01);
(Continued)

(58) Field of Classification Search
CPC .... G01M 3/24; G01M 3/2884; G01N 29/265; G01N 29/24; G01N 29/225; G01N 2291/105; G01N 2291/106; G01N 2291/23636; G21C 17/01; G21C 17/003; G21C 17/017

USPC ........ 73/865.8, 584, 587–588, 648, 622–623, 73/661, 634

See application file for complete search history.

(56) References Cited

U.S. PATENT DOCUMENTS 3,600,613 A    8/1971 Clarke
4,117,733 A *  10/1978 Gugel .............................. 73/634
(Continued)

FOREIGN PATENT DOCUMENTS

EP    0 017 744 A1    10/1980
JP    02-291957 A     12/1990
(Continued)

OTHER PUBLICATIONS

International Search Report for PCT/JP2012/054133, mailing date of May 22, 2012; With English translation.
(Continued)

*Primary Examiner* — Eric S McCall
*Assistant Examiner* — Anthony W Megna Fuentes
(74) *Attorney, Agent, or Firm* — Westerman, Hattori, Daniels & Adrian, LLP

(57) ABSTRACT

A pipe processing device provided with a subject insertion body (1) includes an insertion end portion (2) that is provided on a front side of the subject insertion body inserted into the pipe and is formed on an outer diameter smaller than an inner diameter of the pipe, an axial ultrasonic sensor (21) that transmits and receives a sonic wave in an insertion direction with respect to a front end of the insertion end portion, a radial ultrasonic sensor (22) that transmits and receives a sonic wave in a direction intersecting a center axis at a side portion of the insertion end portion, and a control unit that controls the movement mechanism according to detection results of the axial ultrasonic sensor and the radial ultrasonic sensor.

12 Claims, 16 Drawing Sheets

(51) Int. Cl.
  *G01N 29/26* (2006.01)
  *G01N 29/265* (2006.01)
  *G01N 29/22* (2006.01)
  *F22B 37/00* (2006.01)
  *G21C 17/017* (2006.01)
  *G01B 17/00* (2006.01)

(52) U.S. Cl.
  CPC ............ *G01N 29/225* (2013.01); *G01N 29/265* (2013.01); *G21C 17/017* (2013.01); *G01N 2291/267* (2013.01); *G01N 2291/2636* (2013.01)

(56) References Cited

U.S. PATENT DOCUMENTS

| | | | | |
|---|---|---|---|---|
| 4,131,018 | A | * | 12/1978 | Muller et al. ................ 73/866.5 |
| 4,196,049 | A | | 4/1980 | Burns et al. |
| 2011/0314918 | A1 | * | 12/2011 | Kawanami ............ G01N 29/07 73/623 |

FOREIGN PATENT DOCUMENTS

| | | |
|---|---|---|
| JP | 03-033651 A | 2/1991 |
| JP | 06-088809 A | 3/1994 |
| JP | 08-211034 A | 8/1996 |
| JP | 2010-122175 A | 6/2010 |

OTHER PUBLICATIONS

Written Opinion of PCT/JP2012/054133, mailing date of May 22, 2012.

Extended European Search Report dated Dec. 2, 2014, issued in corresponding EP application No. 12767551.9. (8 pages).

Decision of Patent Grant dated Feb. 10, 2015, issued in corresponding Japanese Patent Application No. 2011-083116, with partial English translation (3 pages).

* cited by examiner

PIPE PROCESSING DEVICE AND PIPE PROCESSING METHOD

FIELD

The present invention relates to, for example, a pipe processing device and a pipe processing method for inspecting or processing a pipe, and more particularly, to a pipe processing device and a pipe processing method capable of disposing the processing device at the center of the pipe with high precision.

BACKGROUND

For example, in nuclear paraphernalia, a pipe is regularly inspected by an inspection device in order to ensure safety and reliability thereof. Then, when a surface defect such as a crack caused by a secular change occurs or when it is determined that a surface defect caused by a secular change occurs at a welding portion of a nozzle of the pipe as a result of the inspection, there is a need to cut or repair a concerned portion by a processing device. Such a processing device that inspects or processes the pipe is inserted from an opening portion of the pipe as a subject, but it is preferable to insert the processing device so that the processing device passes through the center of the pipe in order to inspect or process the pipe with high precision. In the nuclear paraphernalia, since the pipe is inspected or processed under a radiation environment, it is preferable to move the processing device by a remote operation in consideration of safety, but particularly, in a pipe with a relatively small diameter, it is difficult to insert the processing device so that the processing device passes through the center of the pipe by the remote operation.

In the related art, for example, a pipe inspecting device and a pipe inspecting method described in Patent Literature 1 are simply used to accurately dispose an ultrasonic sensor at the center of the pipe to detect a flaw with high precision. Then, in the device which includes an ultrasonic sensor, a driving unit, a position control unit, and an ultrasonic transmission and reception control unit and detects a flaw in a substantially cylindrical pipe, the sensor is disposed such that the pipe axis matches the sensor rotation axis and is rotated while scanning the pipe so as to detect a flaw on a pipe inner face in the radial direction. Here, the device further includes a position correcting unit which calculates the position of the pipe axis based on an ultrasonic signal, an ultrasonic propagation time, and position information of the sensor obtained by the scanning of the sensor while transmitting an ultrasonic wave in a direction perpendicular to the axis from the sensor disposed at a position assumed as the axis of the pipe before detecting the flaw and generates and transmits a control signal for correcting the position of the sensor to the position of the calculated pipe axis.

CITATION LIST

Patent Literature

Patent Literature 1: Japanese Laid-open Patent Publication No. 2010-122175

SUMMARY

Technical Problem

In the pipe inspecting device and the pipe inspecting method described in Patent Literature 1, the ultrasonic sensor for detecting a flaw is used as the ultrasonic sensor that obtains the position information for calculating the position of the pipe axis. For this reason, the ultrasonic sensor is disposed to face the pipe inner face. That is, the pipe inspecting device described in Patent Literature 1 does not include any means for obtaining the position information of the pipe and any guidance for inserting the device into the opening portion when inserting the device into the pipe.

The invention has been made to solve the problems described above, and an object of the invention is to provide a pipe processing device and a pipe processing method capable of guiding the pipe processing device into a pipe for insertion and guiding the pipe processing device for insertion so that the pipe processing device passes through the center of the pipe.

Solution to Problem

According to an aspect of the present invention, a pipe processing device provided with an subject insertion body, which is inserted into a pipe from an opening portion of the pipe, to be movable by a movement mechanism in an axial direction along a center axis of the subject insertion body, a radial direction perpendicular to the center axis, a rotation direction of rotating about the center axis, and an oblique direction oblique with respect to the center axis, the pipe processing device includes: an insertion end portion that is provided on a front side of the subject insertion body to be inserted into the pipe and is formed in a smaller outer diameter than an inner diameter of the pipe; an axial ultrasonic sensor that transmits and receives a sonic wave in an insertion direction with respect to a front end of the insertion end portion; a radial ultrasonic sensor that transmits and receives a sonic wave in a direction intersecting the center axis at a side portion of the insertion end portion; and a control unit that controls the movement mechanism according to detection results of the axial ultrasonic sensor and the radial ultrasonic sensor.

According to the pipe processing device, the subject insertion body is disposed at a position of detecting a distance from the outer edge of the opening portion of the pipe by the axial ultrasonic sensor; the subject insertion body is moved in a radial direction to a position where the distance detected by the axial ultrasonic sensor is larger than the outer edge of the opening portion of the pipe; the subject insertion body is moved in an axial direction to a position where an inner face of the pipe is detected by the radial ultrasonic sensor; a distance from the inner face of the pipe is detected by the radial ultrasonic sensor while rotating the subject insertion body in a rotation direction, and the subject insertion body is moved in a radial direction to a position where the distance is the same; the subject insertion body is moved in an axial direction by a predetermined distance, a distance from the inner face of the pipe is detected by the radial ultrasonic sensor while rotating the subject insertion body in a rotation direction, and the subject insertion body is moved in a radial direction to a position where the distance is the same; and the subject insertion body is moved in an oblique direction to a position where the center axis matches a line connecting two points with the same distance from the inner face of the pipe and the subject insertion body is moved in an axial direction to insert the subject insertion body into the pipe. For this reason, the subject insertion body is inserted into the pipe with the center axis matching the center axis of the pipe. As a result, it is possible to guide the subject insertion body into the pipe for insertion and to guide the subject insertion body for insertion so that the subject insertion body passes through the center of the pipe.

Advantageously, in the pipe processing device, the insertion end portion is formed to be tapered toward the front side.

According to the pipe processing device, the subject insertion body is moved in the axial direction to the position where the inner face of the pipe is detected by the radial ultrasonic sensor, the distance from the inner face of the pipe is detected by the radial ultrasonic sensor while rotating the subject insertion body in the rotation direction, the subject insertion body is moved in the radial direction to the position where the distance is the same, the subject insertion body is moved in the axial direction by the predetermined distance, the distance from the inner face of the pipe is detected by the radial ultrasonic sensor while rotating the subject insertion body in the rotation direction, the subject insertion body is moved in the radial direction to the position where the distance is the same, and the subject insertion body is moved in the oblique direction to the position where the center axis matches the line connecting two points with the same distance from the inner face of the pipe. In this case, it is possible to prevent the insertion end portion from coming in contact with the inner face of the pipe. As a result, it is possible to move the subject insertion body to the more accurate position.

Advantageously, the pipe processing device further includes a sensor support portion that is provided on the side portion of the subject insertion body and in which a plurality of inspection ultrasonic sensors transmitting and receiving a sonic wave in a direction intersecting the center axis is disposed along the center axis. A plurality of the sensor support portions is provided at symmetrical positions about the center axis.

According to the pipe processing device, it is possible to move the inspection ultrasonic sensor along the pipe inner face and to inspect the pipe with high precision.

Advantageously, in the pipe processing device, the sensor support portions are supported to be slidable in a radial direction perpendicular to the center axis, and are elastically biased in a protrusion direction.

According to the pipe processing device, since the sensor support portion comes in contact with the inner face of the pipe, it is possible to move the inspection ultrasonic sensor while coming in contact with the pipe inner face and to inspect the pipe with high precision. In addition, since the sensor support portion is moved in the radial direction along the unevenness of the pipe inner face, it is possible to allow the inspection ultrasonic sensor to follow the shape of the pipe inner face and to inspect the pipe with high precision.

Advantageously, in the pipe processing device, the sensor support portions are supported to be tiltable in a front and back direction of insertion.

According to the pipe processing device, since the sensor support portion is moved in the front and back direction along the unevenness of the pipe inner face, it is possible to allow the inspection ultrasonic sensor to follow the shape of the pipe inner face and to inspect the pipe with high precision.

Advantageously, in the pipe processing device, the sensor support portions supported to be tiltable in the front and back direction are elastically biased in the front direction.

According to the pipe processing device, since the front side of the subject insertion body is tapered so that the sensor support portion is inclined to the front side when the subject insertion body is inserted into the pipe, it is possible to smoothly perform the insertion of the subject insertion body.

Advantageously, in the pipe processing device, the sensor support portions are supported to be tiltable in a circumferential direction.

According to the pipe processing device, since the sensor support portion is moved in the circumferential direction along the unevenness of the pipe inner face, it is possible to allow the inspection ultrasonic sensor to follow the shape of the pipe inner face and to inspect the pipe with high precision.

Advantageously, in the pipe processing device, at least three inspection ultrasonic sensors are disposed along the center axis with respect to the sensor support portions, and the inspection ultrasonic sensor positioned on the intermediate side is supported to be slidable in a protrusion direction from an outer face of the sensor support portion and is elastically biased in the protrusion direction.

Since a plurality of sonic waves is transmitted and received at different angles due to arranging a plurality of inspection ultrasonic sensors, precision in detection is improved. When at least three inspection ultrasonic sensors are disposed, the inspection ultrasonic sensor on the intermediate side may be separated from the pipe inner face by the unevenness of the pipe inner face. From this point, according to the pipe processing device, since the inspection ultrasonic sensor positioned on the intermediate side is elastically biased to protrude from the outer face of the sensor support portion, the inspection ultrasonic sensor positioned on the intermediate side is prevented from being separated from the pipe inner face by the unevenness of the pipe inner face, and hence it is possible to inspect the pipe with high precision.

Advantageously, in the pipe processing device, a plurality of protrusion portions provided to protrude on the side portion of the subject insertion body is provided at symmetrical positions about the center axis, is supported to be slidable in a radial direction perpendicular to the center axis, and is elastically biased in a protrusion direction.

According to the pipe processing device, since the protrusion portion is moved in the radial direction along the unevenness of the pipe inner face while coming in contact with the pipe inner face, it is possible to keep the state where the center axis matches the center axis of the pipe.

Advantageously, in the pipe processing device, the protrusion portions are equally disposed in a circumferential direction about the center axis as a reference along with the sensor support portions.

According to the pipe processing device, since each protrusion portion and each sensor support portion are equally disposed in the circumferential direction in the pipe, it is possible to stably keep the state where the center axis matches the center axis of the pipe.

Advantageously, in the pipe processing device, at least one outer corner of the subject insertion body, the insertion end portion, the sensor support portion, or the protrusion portion is arc or chamfered-processed.

According to the pipe processing device, it is possible to smoothly move the device in a case of the insertion of the device into the pipe, the movement of the device in the pipe, and the extraction of the device from the pipe.

According to another aspect of the present invention, a pipe processing method for moving the pipe processing device according to any one of claims 1 to 11 by the movement mechanism to insert the pipe processing device from the opening portion of the pipe into the pipe, the method includes: disposing the subject insertion body at a position of detecting a distance from an outer edge of the opening portion of the pipe by the axial ultrasonic sensor; moving the subject insertion body in a radial direction to a position where the distance detected by the axial ultrasonic sensor is larger than the outer edge of the opening portion of the pipe; moving the subject insertion body in an axial direction to a position where an inner face of the pipe is detected by the radial ultrasonic sensor; detecting a distance from the inner face of the pipe by the radial ultrasonic sensor while rotating the subject insertion body in a rotation direction, and moving the subject insertion body in a radial direction to a position where the distance is the same; moving the subject insertion body in an axial direction by a predetermined distance, detecting a distance from the inner face of the pipe by the radial ultrasonic sensor while rotating the subject insertion body in a rotation direction, and moving the subject insertion body in a radial direction to a position where the distance is the same; and moving the subject insertion body in an oblique direction to a position where the center axis matches a line connecting two points with the same distance from the inner face of the pipe and moving the subject insertion body in an axial direction to insert the subject insertion body into the pipe.

According to the pipe processing method, the subject insertion body is inserted into the pipe while the insertion of the device into the pipe is guided and the center axis of the subject insertion body matches the center axis of the pipe. As a result, it is possible to guide the subject insertion body into the pipe for insertion and to guide the subject insertion body for insertion so that the subject insertion body passes through the center of the pipe.

Advantageous Effects of Invention

According to the invention, it is possible to guide the subject insertion body into the pipe for insertion and to guide the subject insertion body for insertion so that the subject insertion body passes through the center of the pipe.

DESCRIPTION OF EMBODIMENTS

Hereinafter, an embodiment according to the invention will be described in detail with reference to the drawings. In addition, the invention is not limited to the embodiment. In addition, constituents in the following embodiment include a constituent which may be easily replaced by a person skilled in the art or a constituent which has substantially the same configuration.

Figure 1:
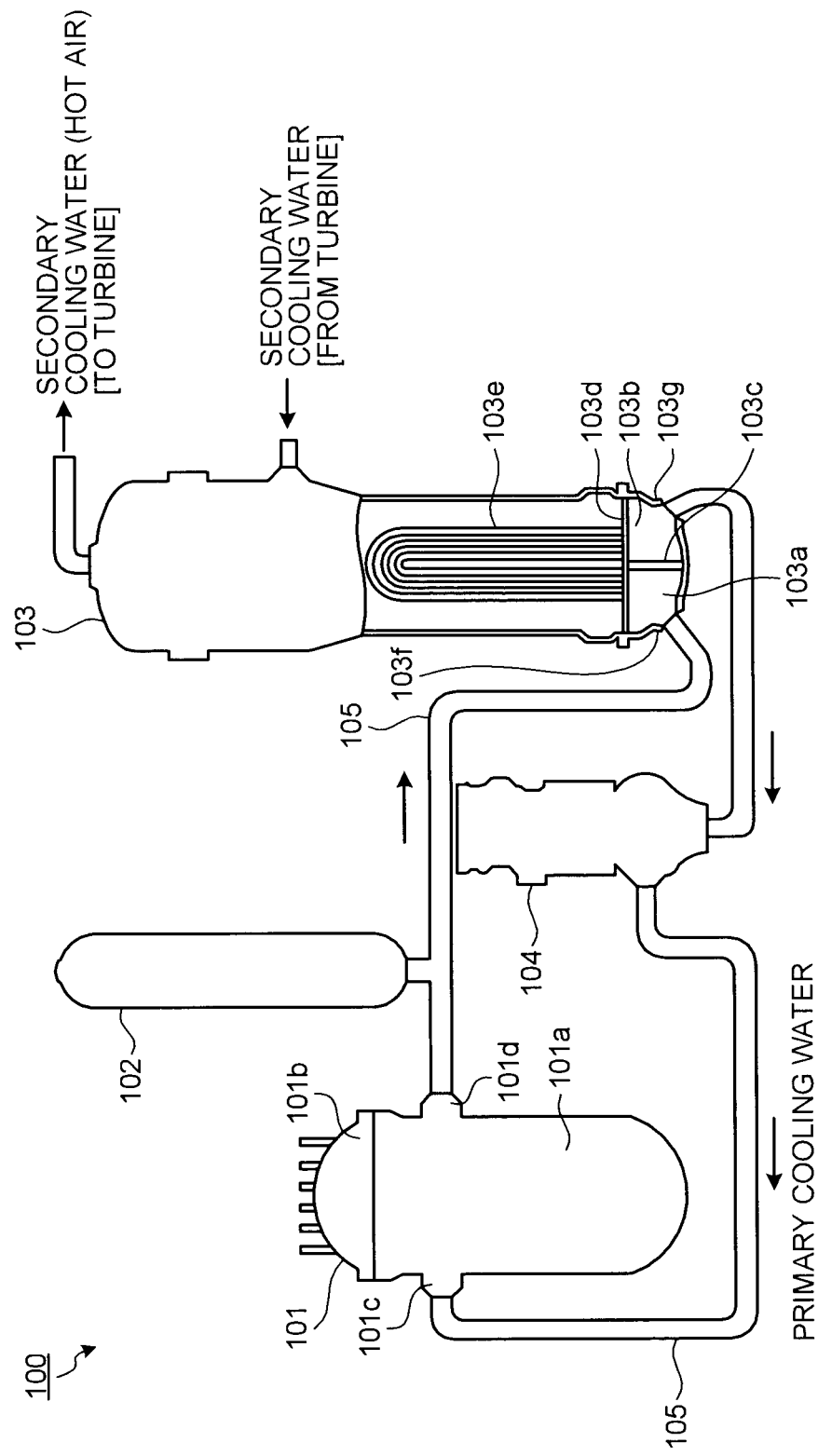
FIG. 1 is a schematic diagram illustrating an example of nuclear paraphernalia.
Figure 2:
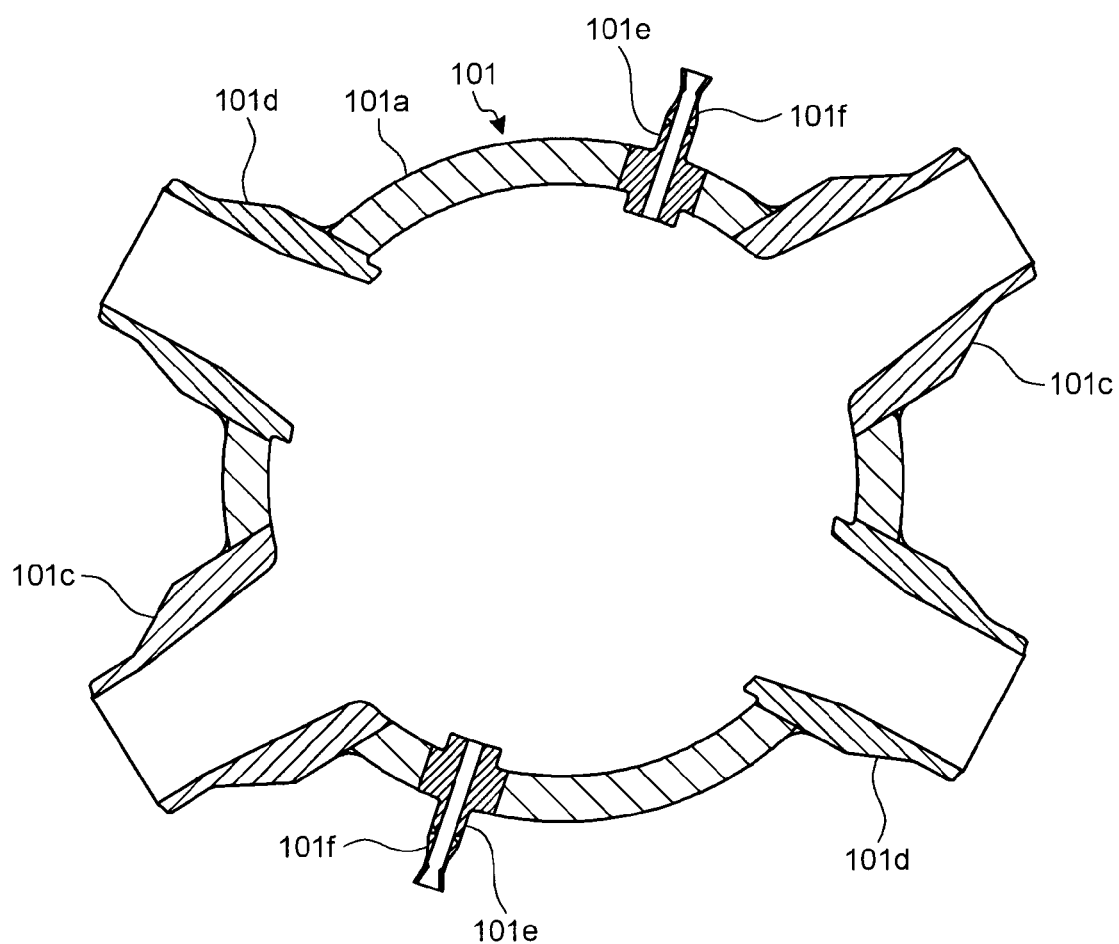
FIG. 2 is a horizontal cross-sectional view of a reactor vessel.

FIG. 1 is a schematic diagram illustrating an example of nuclear paraphernalia, and FIG. 2 is a horizontal cross-sectional view of a reactor vessel. As illustrated in FIG. 1, a nuclear paraphernalia 100 is, for example, a pressurized water reactor (PWR). In the nuclear paraphernalia 100, a reactor vessel 101, a pressurizer 102, a steam generator 103, and a pump 104 are sequentially connected by a primary cooling water pipe 105, to configure a circulation path of primary cooling water. In addition, a circulation path of secondary cooling water is formed between the steam generator 103 and a turbine (not illustrated).

In the nuclear paraphernalia 100, the primary cooling water is heated in the reactor vessel 101 to a high temperature and a high pressure, is pressurized in the pressurizer 102 to keep the pressure constant, and is supplied to the steam generator 103 through the primary cooling water pipe 105. In the steam generator 103, a heat exchange between the primary cooling water and the secondary cooling water is performed, and thus the secondary cooling water is evaporated to become steam. The secondary cooling water which becomes the steam by the heat exchange is supplied to the turbine. The turbine is driven by the steam of the secondary cooling water. Power of the turbine is transferred to a generator (not illustrated) to produce electric power. The steam provided for the driving of the turbine is condensed into water, which is supplied to the steam generator 103. Meanwhile, the primary cooling water after the heat exchange is recovered in the pump 104 side through the primary cooling water pipe 105.

In the steam generator 103, as illustrated in FIG. 1, an inlet side channel head 103a and an outlet side channel head 103b are partitioned by a divider plate 103c and provided at a lower portion formed in a semispherical shape. The inlet side channel head 103a and the outlet side channel head 103b are partitioned from the upper portion side of the steam generator 103 by a tube sheet 103d provided at a ceiling portion thereof. On the upper portion side of the steam generator 103, an inverted U-shaped heat-transfer tube 103e is provided. The end portion of the heat-transfer tube 103e is supported by the tube sheet 103d to connect the inlet side channel head 103a and the outlet side channel head 103b. In addition, the inlet side channel head 103a is provided with an inlet nozzle 103f as a pipe nozzle, and the inlet nozzle 103f is connected to the primary cooling water pipe 105 on the inlet side. Meanwhile, the outlet side channel head 103b is provided with an outlet nozzle 103g as a pipe nozzle, and the outlet nozzle 103g is connected to the primary cooling water pipe 105 on the outlet side.

As illustrated in FIG. 1, the reactor vessel 101 includes a reactor vessel body 101a and a reactor vessel head 101b mounted thereon such that a fuel assembly (not illustrated) is inserted and extracted. The reactor vessel head 101b is provided to be opened and closed to the reactor vessel body 101a. The upper side of the reactor vessel body 101a is opened, and the lower side is formed in a semispherical shape to form a closed cylindrical shape, in which an inlet nozzle 101c and an outlet nozzle 101d for supplying and discharging light water as the primary cooling water are provided at the upper portion thereof. The outlet nozzle 101d is connected to the primary cooling water pipe 105 to communicate with the inlet nozzle 103f of the steam generator 103. In addition, the inlet nozzle 101c is connected to the primary cooling water pipe 105 to communicate with the outlet nozzle 103g of the steam generator 103. In addition, as illustrated in FIG. 2, the reactor vessel 101 is provided with a main water nozzle 101e that is a pipe for main water at a position to be flush with the inlet nozzle 101c and the outlet nozzle 101d in the reactor vessel body 101a. The main water nozzle 101e is welded to a main water pipe 101f that is a pipe.

Figure 3:
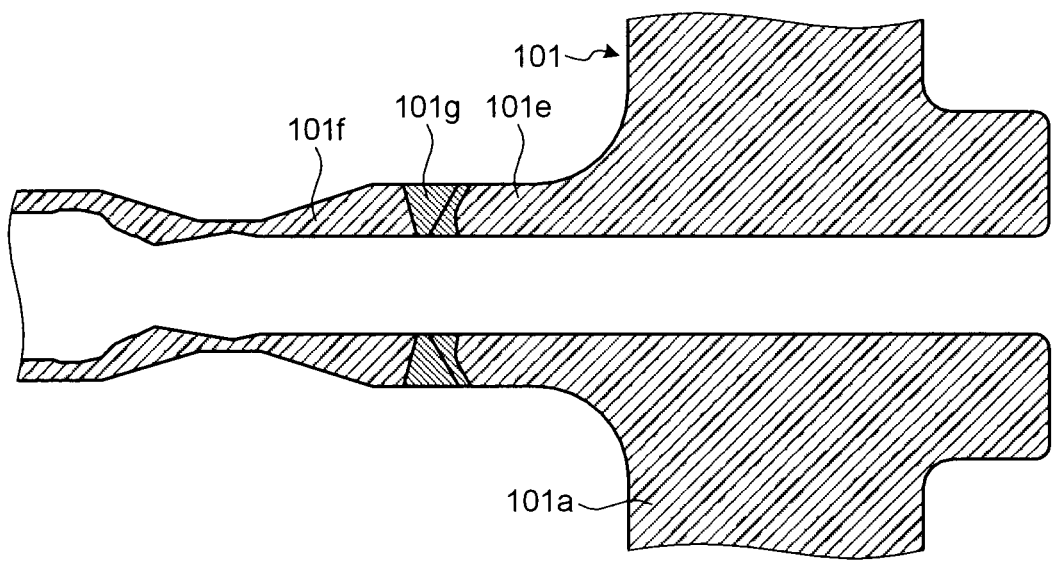
FIG. 3 is a cross-sectional view of a main water nozzle.

FIG. 3 is a cross-sectional view of the main water nozzle. The main water nozzle 101e is regularly inspected to secure safety or reliability of the nuclear paraphernalia 100 described above. As a result of the inspection, as illustrated in FIG. 3, when a surface defect such as a crack caused by the secular change occurs at a welding portion 101g that is a connection portion between the main water nozzle 101e and the main water pipe 101f or when the surface defect caused by the secular change is found, the welding portion 101g is cut or repaired.

Figure 4:
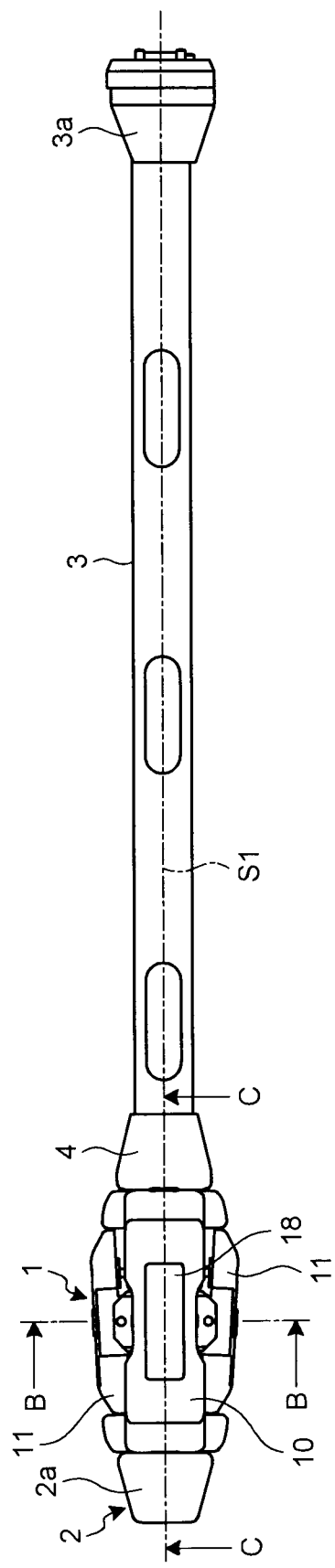
FIG. 4 is an external view of a pipe processing device according to an embodiment of the invention.
Figure 8:
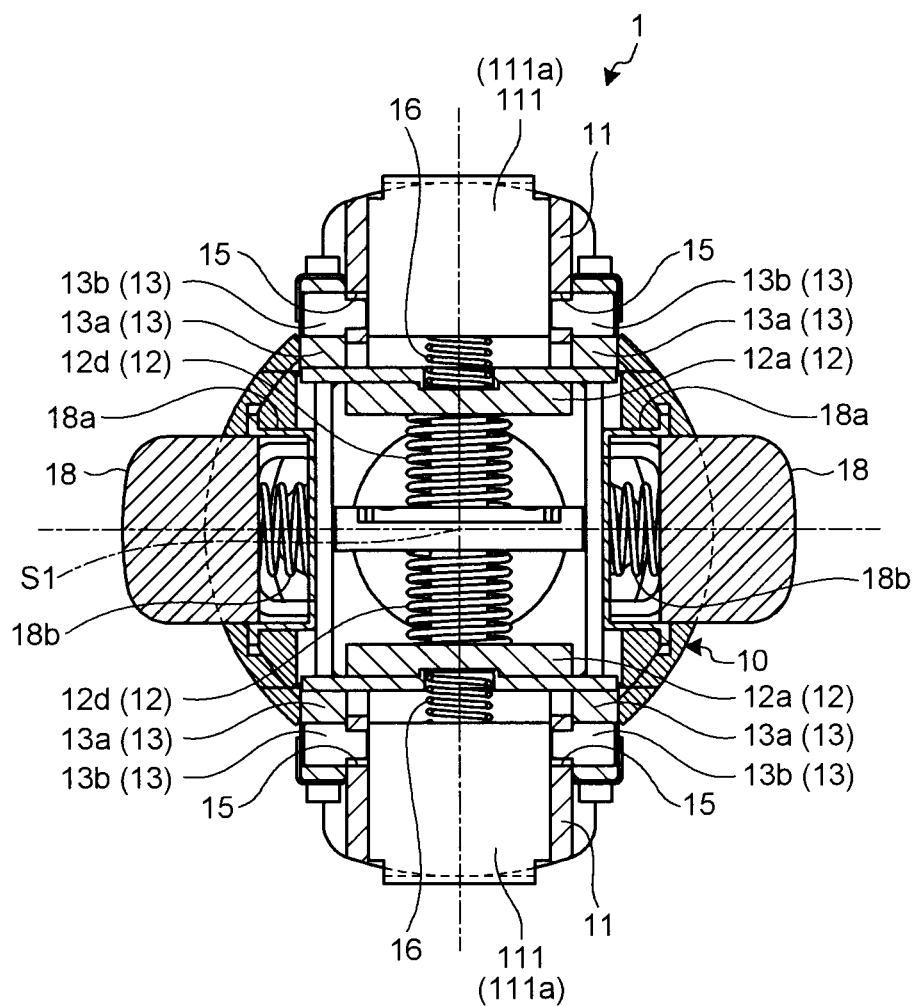
FIG. 8 is a cross-sectional view taken along the line B-B in FIG. 4.
Figure 9:
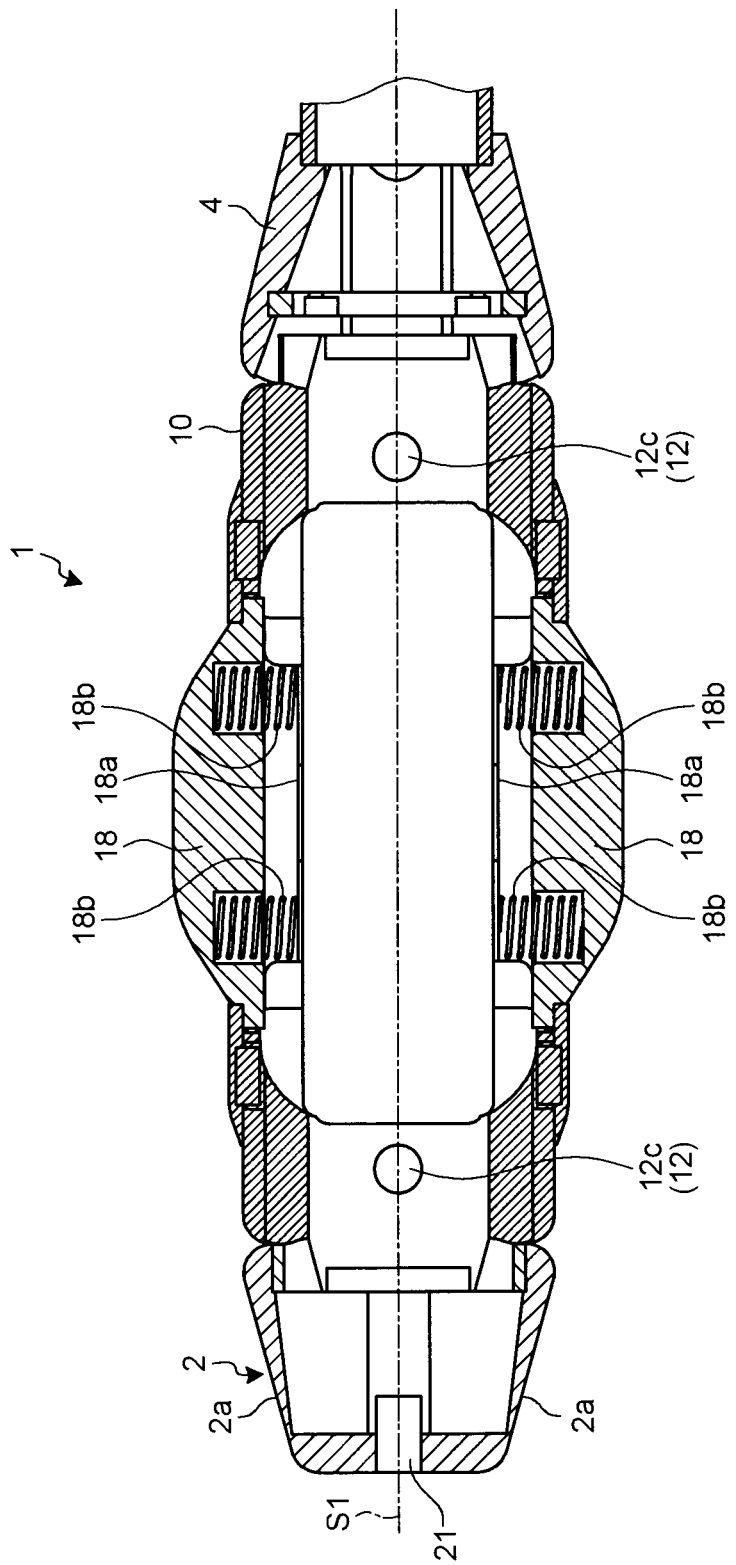
FIG. 9 is a cross-sectional view taken along the line C-C in FIG. 4.

The inspection or the process of cutting and repairing is performed, and thus the pipe processing device according to the embodiment is applied. FIG. 4 is an external view of the pipe processing device according to the embodiment, FIG. 5 is an external view in a state where the pipe processing device illustrated in FIG. 4 is rotated about an axis by 90°, FIG. 6 is an external view of the pipe processing device illustrated in FIG. 4 viewed from the front side, FIG. 7 is a cross-sectional view taken along the line A-A in FIG. 5, FIG. 8 is a cross-sectional view taken along the line B-B in FIG. 4, and FIG. 9 is a cross-sectional view taken along the line C-C in FIG. 4.

Figure 10:
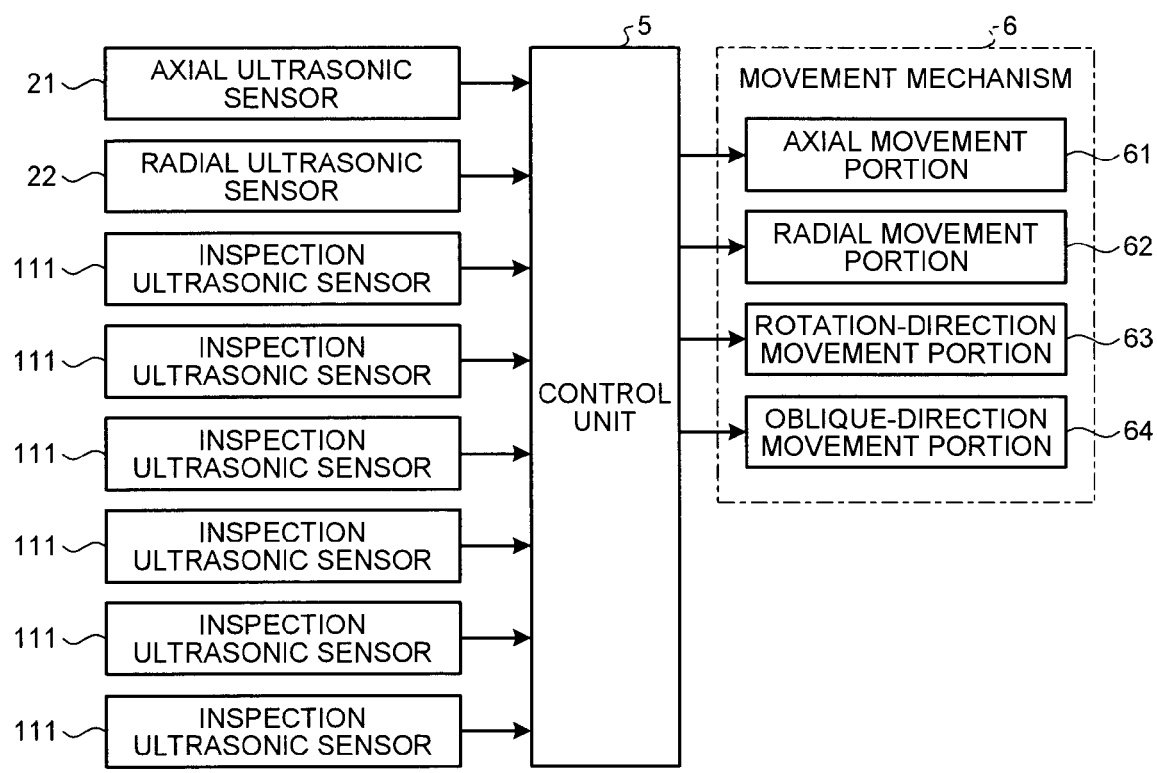
FIG. 10 is a block diagram illustrating a control system of the pipe processing device according to the embodiment of the invention.

The pipe processing device is inserted into the pipe from the main water nozzle 101e to the main water pipe 101f in the reactor vessel 101 described above, and includes an subject insertion body 1, an insertion end portion 2 provided on the front side of the subject insertion body 1 inserted into the pipe, and a fixed portion 3 provided on the back side of the subject insertion body 1 and fixed to a manipulator having a multi-joint structure (not illustrated) as a movement mechanism 6 (see FIG. 10). The insertion end portion 2 is configured as the pipe processing device. In addition, in the pipe processing device, the insertion end portion 2, the subject insertion body 1, and the fixed portion 3 are disposed in this order from the front side of the insertion along the center axis S1. In addition, in the following description, an extending direction of the center axis S1 (a direction taken along the center axis S1) is an axial direction, and a direction perpendicular to the center axis S1 is a radial direction. In addition, a direction of inserting the pipe processing device into the pipe is an insertion direction, a side directed to the insertion direction is a front side, and a reverse direction thereto is a back side.

The insertion end portion 2 is formed with an outer diameter smaller than the inner diameters of the main water nozzle 101e and the main water pipe 101f as the pipe, and has a cylindrical shape based on the center axis S1 as illustrated in FIGS. 4 to 7 and 9. Specifically, the insertion end portion 2 has a tapered face 2a in which the front face is substantially flat and the outer face is inclined toward the front side based on a cone shape based on the center axis S1 to be tapered toward the front side.

Figure 5:
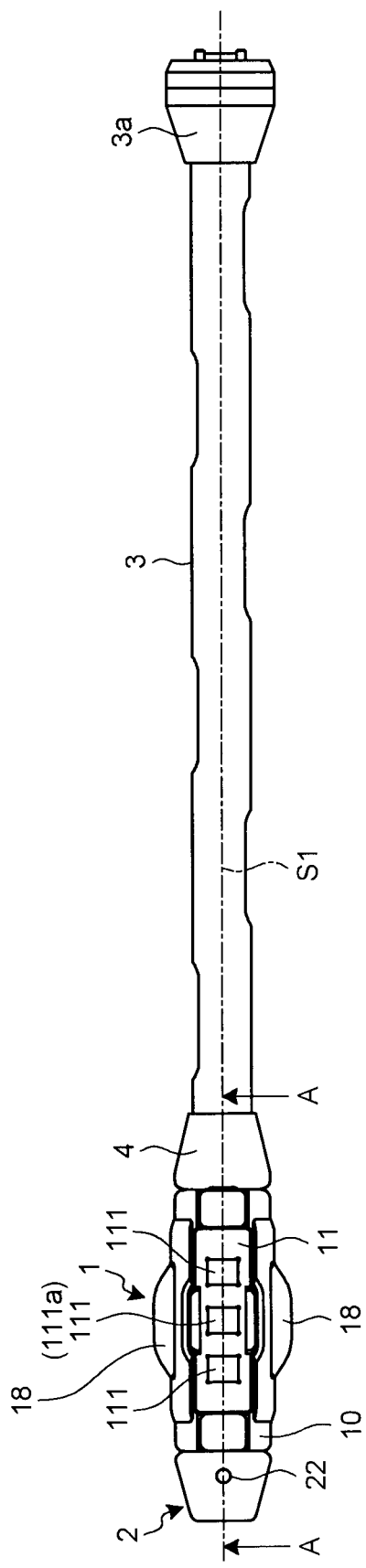
FIG. 5 is an external view while the pipe processing device illustrated in FIG. 4 is rotated about an axis by 90°.
Figure 6:
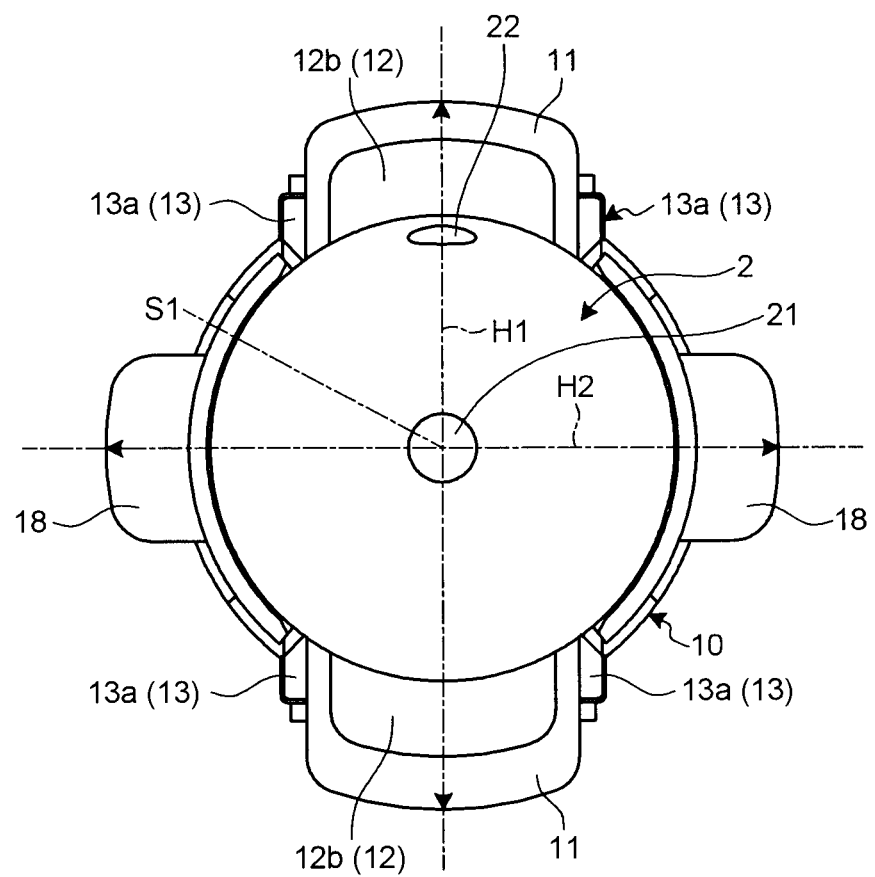
FIG. 6 is an external view when the pipe processing device illustrated in FIG. 4 is viewed from the front side.
Figure 7:
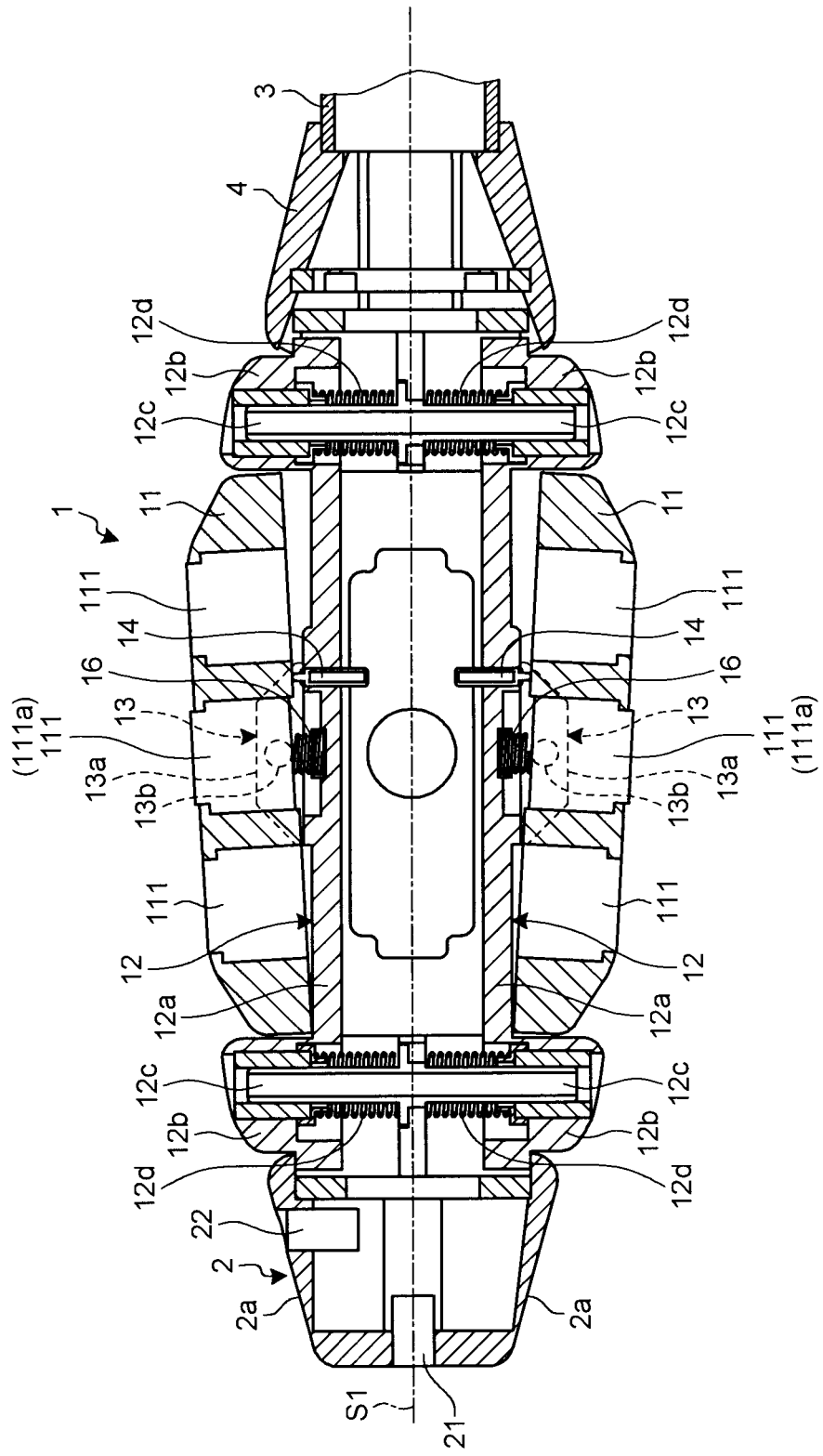
FIG. 7 is a cross-sectional view taken along the line A-A in FIG. 5.

As illustrated in FIGS. 5 to 7, the insertion end portion 2 is provided with an axial ultrasonic sensor 21 and a radial ultrasonic sensor 22. The axial ultrasonic sensor 21 is provided at the front end of the insertion end portion 2, and transmits and receives sonic waves in the insertion direction along the center axis S1. The radial ultrasonic sensor 22 transmits and receives the sonic waves in a direction (the radial direction) intersecting (perpendicular to) the center axis S1.

As illustrated in FIGS. 4 to 6, 8, and 9, the subject insertion body 1 is configured basically with a main body portion 10 having a cylindrical shape based on the center axis S1. The main body portion 10 is formed with an outer diameter smaller than the inner diameters of the main water nozzle 101e and the main water pipe 101f as the pipe.

As illustrated in FIGS. 4 to 8, the subject insertion body 1 has sensor support portions 11. The plurality of sensor support portions 11 is provided at symmetrical positions about the center axis S1 to extend along the axial direction and protrudes on the side portion of the main body portion 10. In the embodiment, two sensor support portions 11 are provided, and are disposed to protrude in opposing directions based on the center axis S1. In addition, although not illustrated in the figures, for example, when three sensor support portions 11 are provided, they are equally disposed in the circumferential direction based on the center axis S1.

The sensor support portion 11 is provided with a plurality of inspection ultrasonic sensors 111 along the axial direction. In the embodiment, one sensor support portion 11 is provided with three inspection ultrasonic sensors 111 along the axial direction. The inspection ultrasonic sensor 111 transmits and receives sonic waves in a direction intersecting with the center axis S1. In addition, when the subject insertion body 1 is inserted into the pipe, the individual inspection ultrasonic sensors 111 transmit and receive the sonic waves at different angles with respect to the direction (the radial direction) perpendicular to the center axis S1. This is because, when the sonic waves are transmitted and received at a single angle, reception sensitivity is decreased when there is a defect in the same direction as the angle, and thus the defect may not be detected. That is, the plurality of sonic waves is transmitted and received at different angles, and thus the detection precision is thereby improved.

In addition, as illustrated in FIG. 7, the subject insertion body 1 has a slide movement portion 12. The slide movement portion 12 has a support member 12a extending along the axial direction. The support member 12a supports the sensor support portion 11. In addition, the slide movement portion 12 has slide portions 12b provided to protrude to the side portion of the main body portion 10 outside both ends of the sensor support portion 11, at both ends of the support member 12a. In addition, the slide movement portion 12 has a slide shaft 12c. The slide shaft 12c extends in the direction perpendicular to the center axis S1 and is fixed to the main body portion 10. The slide portion 12b is slidably inserted into the extending direction of the slide shaft 12c. For this reason, the slide movement portion 12 is provided slidably in the direction perpendicular to the center axis S1 in which the slide shaft 12c extends. That is, the sensor support portion 11 supported by the slide movement portion 12 is provided slidably in the radial direction. In addition, the slide movement portion 12 has a compression coil spring 12d. The compression coil spring 12d is inserted through the slide shaft 12c, and comes in contact with the slide portion 12b. For this reason, the slide movement portion 12 is elastically biased toward the outside of the main body portion 10 in the extending direction of the slide shaft 12c, which is the radial direction, by the compression coil spring 12d. That is, the sensor support portion 11 supported by the slide movement portion 12 is elastically biased in the protruding direction, which is the radial direction, on the outside of the main body portion 10. In addition, the slide movement portion 12 is provided with the slide portions 12b on both ends of the support member 12a. Each slide portion 12b is slidably movable along the slide shaft 12c, and is elastically biased toward the outside of the main body portion 10 by the compression coil spring 12d. For this reason, in the slide movement portion 12, one end side and the other end side in the axial direction are elastically biased to be slidably movable. That is, in the sensor support portion 11, one end side and the other end side in the axial direction are elastically biased to be slidably movable. In addition, a dimension H1 between the outer faces of the sensor support portions 11 elastically biased toward the outside of the main body portion 10 is larger than the inner diameter of the pipe to be inserted.

In addition, as illustrated in FIGS. 7 and 8, the subject insertion body 1 has a tilt movement portion 13. The tilt movement portion 13 has a bearing member 13a erected along both sides of the sensor support portion 11 in the support member 12a, and a rotation shaft 13b extending in the radial direction with respect to the bearing member 13a and inserted into the substantially center of the extending direction of the sensor support portion 11. For this reason, the sensor support portion 11 is supported to be tiltable in the front and back direction of the insertion direction with respect to the slide movement portion 12. In addition, when the slide movement portion 12 is not provided, the tilt movement portion 13 is provided in the main body portion 10, and supports the sensor support portion 11 to be tiltable in the front and back direction of the insertion direction.

In addition, the tilt movement portion 13 has a tilt biasing portion 14. The tilt biasing portion 14 is configured as a spring plunger and is fixed to the support member 12a. The plunger portion comes in contact with the back side of the sensor support portion 11, which is supported by the tilt movement portion 13, in the insertion direction and elastically biases the sensor support portion 11 on the outside of the subject insertion body 1. That is, the sensor support portion 11 supported to be tiltable in the front and back direction of the insertion by the tilt movement portion 13 is elastically biased in the front direction. In addition, when the slide movement portion 12 is not provided, the tilt biasing portion 14 is provided in the main body portion 10 and elastically biases the sensor support portion 11 in the front direction of the insertion.

In addition, as illustrated in FIG. 8, the subject insertion body 1 has a circumferential movement portion 15. The circumferential movement portion 15 is formed such that at least radial inner diameter of a hole on the sensor support portion 11 side through which the rotation shaft 13b is inserted is larger than the outer diameter of the rotation shaft 13b, in the tilt movement portion 13. That is, the sensor support portion 11 is supported movably in the radial direction with respect to the rotation shaft 13b by the circumferential movement portion 15, which is a hole with a large diameter. For this reason, the sensor support portion 11 is allowed to move in the circumferential direction of the center axis S1 with respect to the rotation shaft 13b, and is supported to be tiltable in the circumferential direction. In addition, when the tilt movement portion 13 is not provided, the circumferential movement portion 15 supports the sensor support portion 11 to be tiltable in the circumferential direction by a configuration of a rail extending in the circumferential direction with respect to the support member 12a of the slide movement portion 12, and a slider slid with the rail although not illustrated in the figures. In addition, when the slide movement portion 12 is not provided, the circumferential movement portion 15 supports the sensor support portion 11 to be tiltable in the circumferential direction with respect to the tilt movement portion 13 provided in the main body portion 10 as described above. In addition, the tilt movement portion 13 and the slide movement portion 12 are not provided, the circumferential movement portion 15 supports the sensor support portion 11 to be tiltable in the circumferential direction by a configuration of a rail extending in the circumferential direction with respect to the main body portion 10, and a slider slid with the rail.

In addition, the sensor support portion 11 has a sensor extrusion portion 16. The sensor extrusion portion 16 is provided when at least three inspection ultrasonic sensors 111 are disposed along the center axis S1, and supports an inspection ultrasonic sensor 111a positioned on the intermediate side to protrude from the outer face in the radial direction and to be slidable with respect to the sensor support portion 11. The sensor extrusion portion 16 is configured as the compression coil spring elastically biasing the inspection ultrasonic sensor 111a on the outside. In addition, in the inspection ultrasonic sensor 111a, slide movement is restricted with respect to the sensor support portion 11 so as not to come out of the outside of the sensor support portion 11.

In addition, as illustrated in FIGS. 4 to 6, 8, and 9, the subject insertion body 1 has protrusion portions 18. The plurality of protrusion portions 18 is provided to protrude in the radial direction on the side portion of the subject insertion body 1 and at symmetrical positions about the center axis S1. In the embodiment, two protrusion portions 18 are provided, and are disposed to protrude in the opposing direction based on the center axis S1. In addition, although not illustrated in the figures, for example, when three protrusion portions 18 are provided, they are equally disposed in the circumferential direction based on the center axis S1. The protrusion portions 18 are provided to be slidably movable in the radial direction by a slide support portion 18a, with respect to the main body portion 10. In addition, the protrusion portions 18 are elastically biased in the direction protruding in the radial direction, which is the slide direction, by a compression coil spring 18b. In addition, as illustrated in FIG. 9, a plurality (two in the embodiment) of compression coil springs 18b are provided in the axial direction. For this reason, the protrusion portion 18 can be tilted and moved back and forth in the axial direction while being elastically biased. In addition, a dimension H2 between the outer faces of the protrusion portions 18 elastically biased toward the outside of the main body portion 10 is larger than the inner diameter of the pipe to be inserted.

In addition, it is preferable that the protrusion portions 18 be equally disposed in the circumferential direction based on the center axis S1 with the sensor support portion 11.

In addition, in the pipe processing device, at least one of outer corners of the subject insertion body 1, the insertion end portion 2, the sensor support portion 11, or the protrusion portion 18 is arc- or chamfered-processed.

In addition, the fixed portion 3 is provided through a joint portion 4 having a shape in which the front and back of the insertion end portion 2 are reversed, on the back side of the subject insertion body 1. The fixed portion 3 is a pipe-shaped member extending backward, and is formed with a diameter smaller than the outer diameter of the front end of the insertion end portion 2 formed to be tapered. A connection portion 3a of the back end of the fixed portion 3 is mounted on the movement mechanism 6. For this reason, the pipe processing device is moved in the axial direction along the center axis S1, in the radial direction perpendicular to the axial direction, in the rotation direction of rotating around the center axis S1, and in the oblique direction oblique with respect to the center axis S1, by the movement mechanism 6.

FIG. 10 is a block diagram of a control system of the pipe processing device according to the embodiment, and FIGS.

11 to 16 are diagrams illustrating an insertion process of the pipe processing device according to the embodiment.

As illustrated in FIG. 10, in the pipe processing device described above, the axial ultrasonic sensor 21 and the radial ultrasonic sensor 22 described above are connected to a control unit 5. In addition, in the pipe processing device, the inspection ultrasonic sensors 111 described above are connected to the control unit 5. In addition, in the pipe processing device, the movement mechanism 6 moving the pipe processing device is connected. As described above, the movement mechanism 6 is configured as the manipulator with the multi-joint structure, and includes an axial movement portion 61 moving the pipe processing device in the axial direction, a radial movement portion 62 moving the pipe processing device in the radial direction, a rotation-direction movement portion 63 moving the pipe processing device in the rotation direction, and an oblique-direction movement portion 64 moving the pipe processing device in the oblique direction. The axial movement portion 61, the radial movement portion 62, the rotation-direction movement portion 63, and the oblique-direction movement portion 64 are connected to the control unit 5.

The control unit 5 is configured by a microcomputer or the like, and controls the axial movement portion 61, the radial movement portion 62, the rotation-direction movement portion 63, and the oblique-direction movement portion 64 of the movement mechanism 6, according to detection results of the axial ultrasonic sensor 21 and the radial ultrasonic sensor 22. In addition, the control unit 5 inputs the detection result of each inspection ultrasonic sensor 111, and stores inspection information of the pipe.

Specifically, an operation of the pipe processing device by the control unit 5 will be described. Herein, in order to secure safety or reliability of the nuclear paraphernalia 100 described above, a process of inspecting the welding portion 101g that is the connection portion between the main water nozzle 101e and the main water pipe 101f in the reactor vessel 101 will be described. The inside of the pipes (the main water nozzle 101e and the main water pipe 101f) that are the inspection subject is in a state filled with water, and the movement mechanism 6 and the pipe processing device mounted on the movement mechanism 6 are disposed in the water. In addition, the position information of the pipe and the internal structure information of the pipe are stored in advance in the control unit 5 and the movement mechanism 6 moves the pipe processing device basically based on the information stored in the control unit 5.

Figure 11:
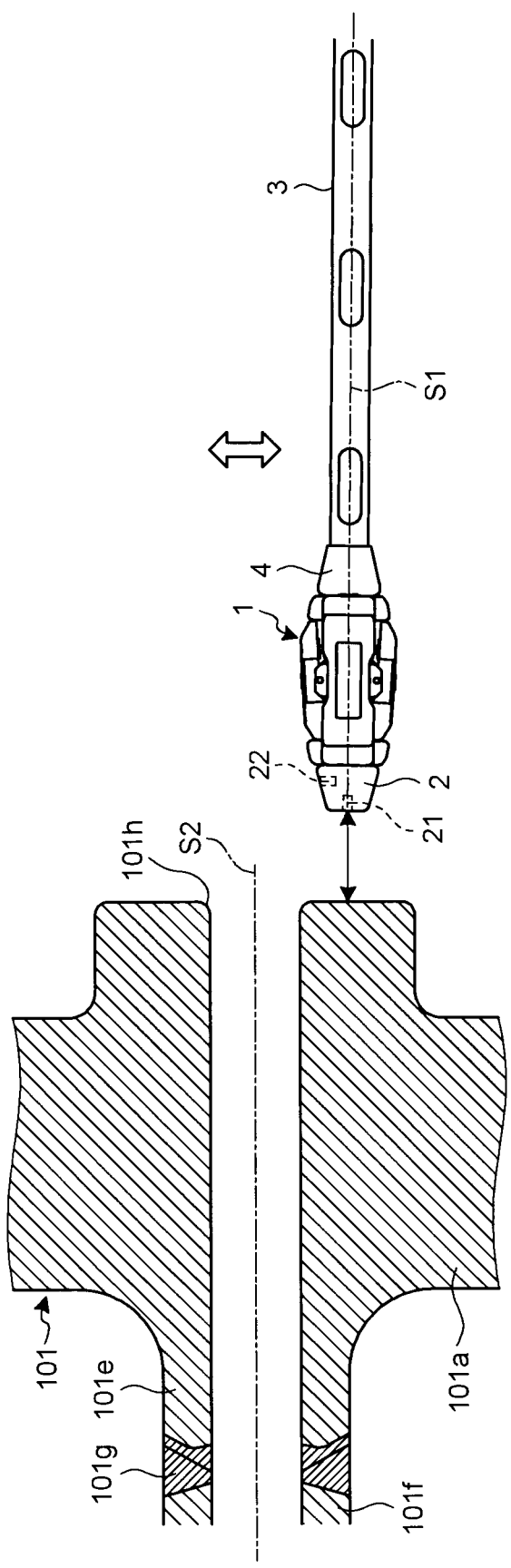
FIG. 11 is a diagram illustrating an insertion process of the pipe processing device according to the embodiment of the invention.

First, as illustrated in FIG. 11, the subject insertion body 1 is disposed at a position for detecting the distance from the outer edge of an opening portion 101h of the pipe by the axial ultrasonic sensor 21. The axial ultrasonic sensor 21 detects the distance from the outer edge of the opening portion 101h of the pipe, and thus it is possible to recognize the position of the pipe processing device with respect to the outer edge of the opening portion 101h of the pipe.

Figure 12:
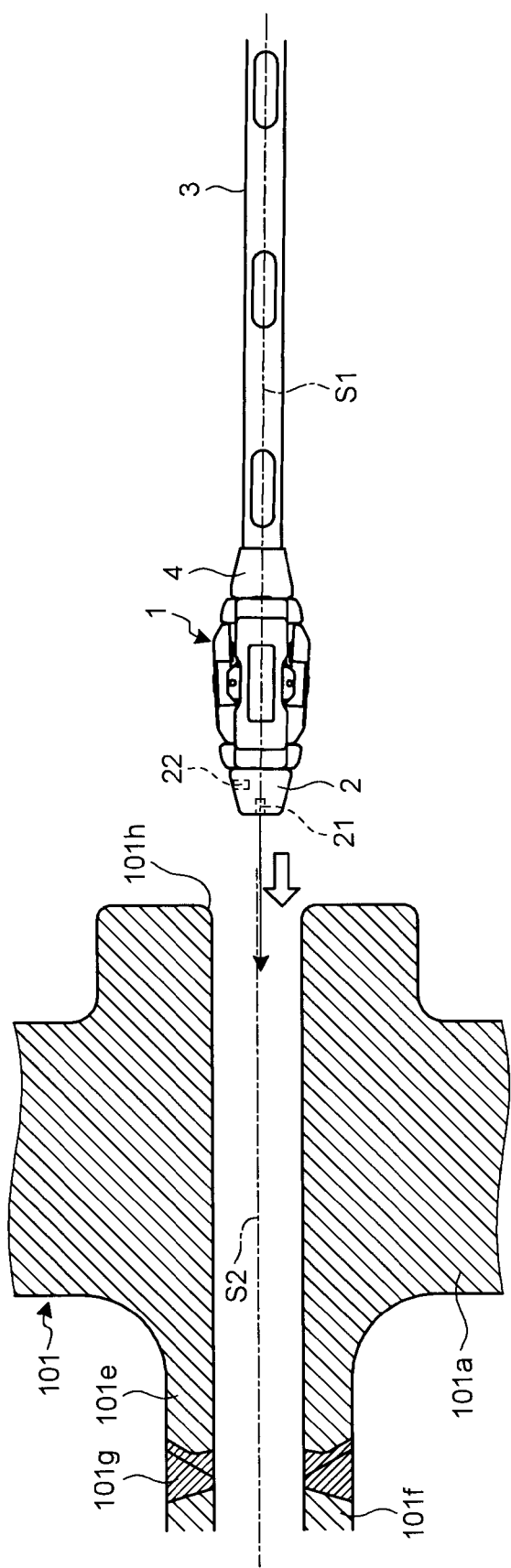
FIG. 12 is a diagram illustrating an insertion process of the pipe processing device according to the embodiment of the invention.

Then, as illustrated in FIG. 12, the subject insertion body 1 is moved in the radial direction from the position of FIG. 11 to the position where the distance detected by the axial ultrasonic sensor 21 is larger than the outer edge of the opening portion 101h of the pipe. That the distance is larger than the outer edge of the opening portion 101h of the pipe means that the opening portion 101h of the pipe is detected. That is, the axial ultrasonic sensor 21 detects the distance larger than the outer edge of the opening portion 101h of the pipe, and thus it is possible to recognize the opening portion 101h of the pipe. The center axis S1 of the subject insertion body 1 is aligned with the position of the center axis S2 of the pipe based on the position information of the pipe stored in advance. Herein, since it is difficult to confirm the accurate position of the center axis S2 of the pipe, the center axis S1 of the subject insertion body 1 may not coincide with the center axis S2 of the pipe.

Figure 13:
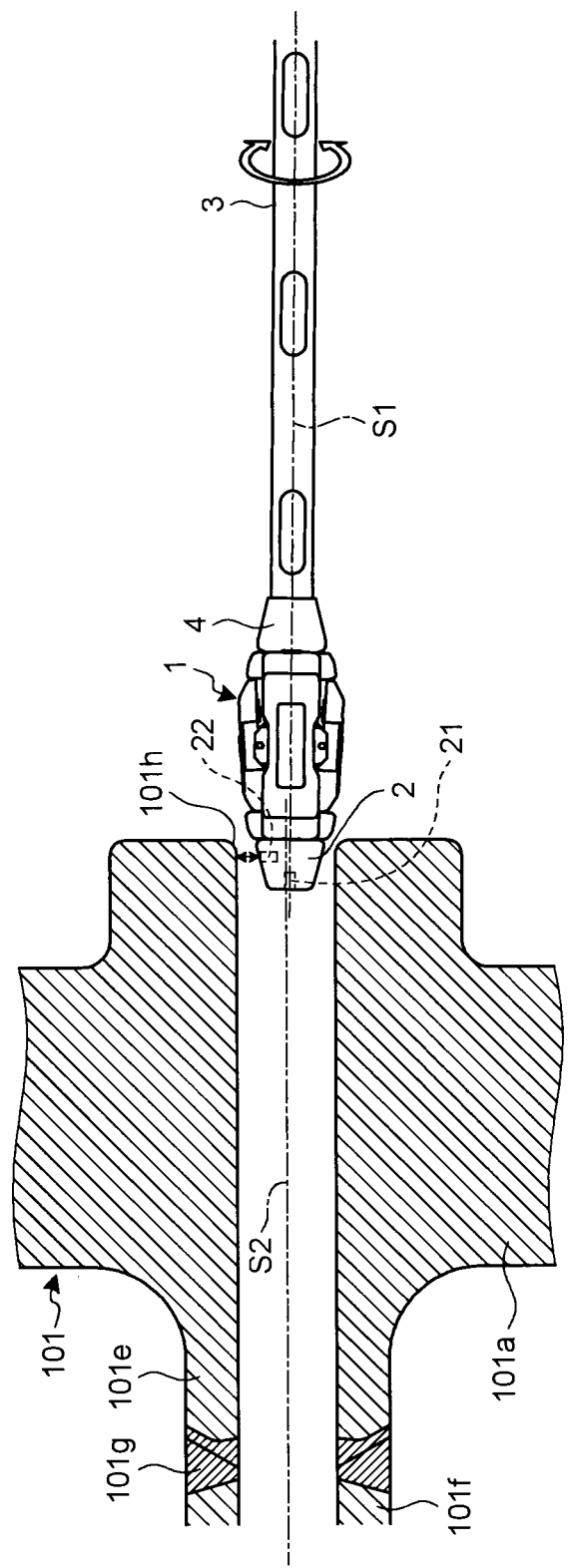
FIG. 13 is a diagram illustrating an insertion process of the pipe processing device according to the embodiment of the invention.

Then, as illustrated in FIG. 13, the subject insertion body 1 is moved in the axial direction from the position of FIG. 12 to the position where the inner face of the pipe is detected by the radial ultrasonic sensor 22. The insertion end portion 2 provided with the radial ultrasonic sensor 22 has the diameter smaller than the inner diameter of the pipe, and is formed to be tapered. In addition, at the position where the inner face of the pipe is detected by the radial ultrasonic sensor 22, the subject insertion body 1 has not been inserted into the pipe yet. For this reason, the insertion end portion 2 and the subject insertion body 1 do not come in contact with the pipe.

Figure 14:
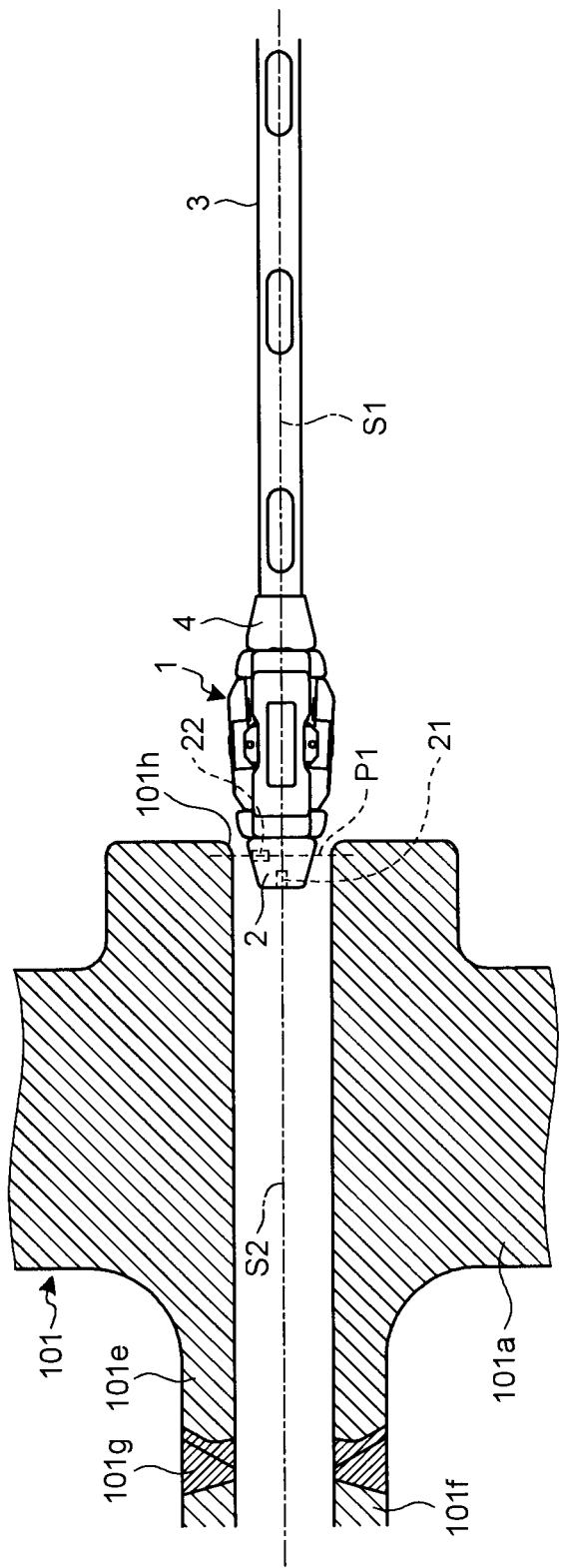
FIG. 14 is a diagram illustrating an insertion process of the pipe processing device according to the embodiment of the invention.

Then, as illustrated in FIG. 14, at the position of FIG. 13, the distances from the inner face of the pipe are detected by the radial ultrasonic sensor 22 while rotating the subject insertion body 1 in the rotation direction. The subject insertion body 1 is moved in the radial direction to the position where the distances are the same. Herein, when the cross section of the pipe is circular, the subject insertion body 1 is moved in the radial direction to the position where all the distances are the same. In addition, when the cross section of the pipe is elliptical, the subject insertion body 1 is moved in the radial direction to the position where the distances opposing each other are the same. For this reason, a detection point P1 by the radial ultrasonic sensor 22 on the center axis S1 of the subject insertion body 1 coincides with the center axis S2 of the pipe.

Figure 15:
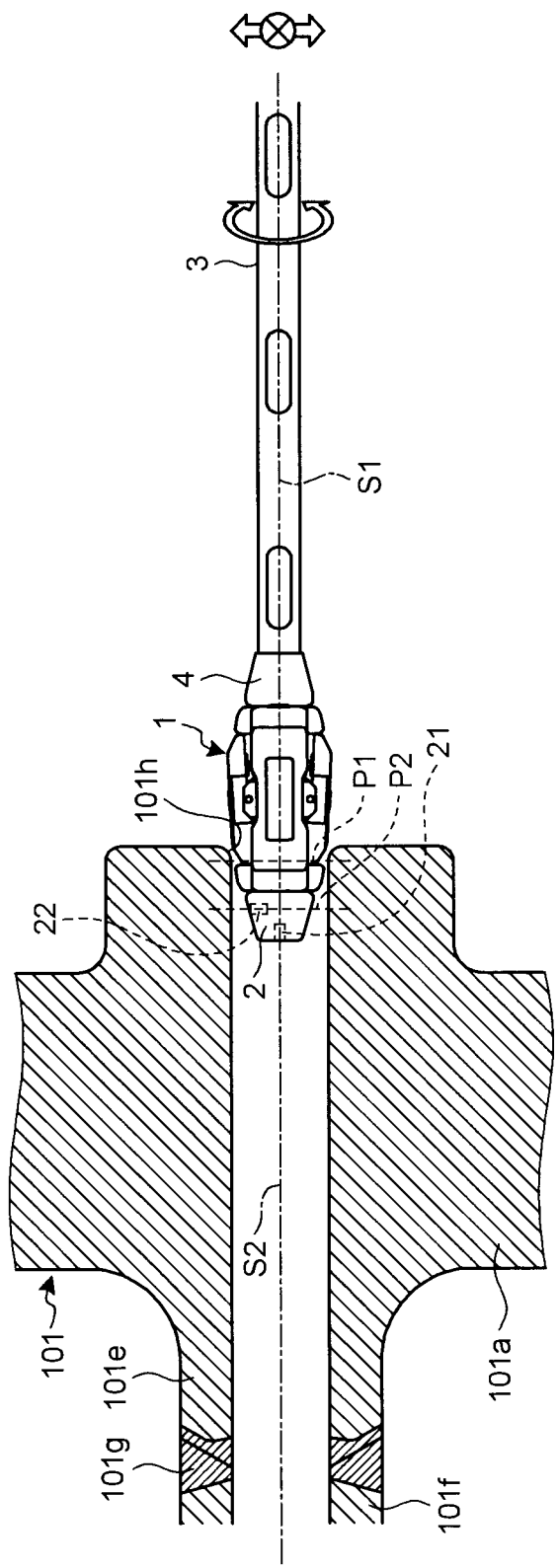
FIG. 15 is a diagram illustrating an insertion process of the pipe processing device according to the embodiment of the invention.

Then, as illustrated in FIG. 15, the subject insertion body 1 is moved in the axial direction by a predetermined distance from the position of FIG. 14, and then the distances from the inner face of the pipe are detected by the radial ultrasonic sensor 22 while rotating the subject insertion body 1 in the rotation direction. The subject insertion body 1 is moved in the radial direction to the position where the distances are the same. Herein, the predetermined distance means a range in which the subject insertion body 1 has not been inserted into the pipe yet. For this reason, a detection point P2 by the radial ultrasonic sensor 22 on the center axis S1 of the subject insertion body 1 coincides with the center axis S2 of the pipe.

Figure 16:
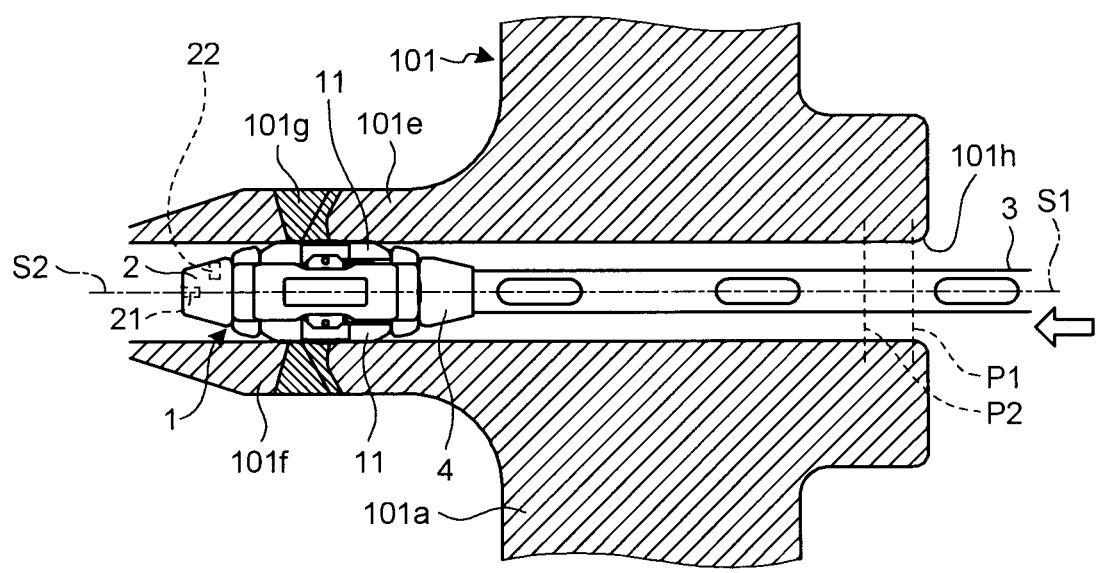
FIG. 16 is a diagram illustrating an insertion process of the pipe processing device according to the embodiment of the invention.

Then, as illustrated in FIG. 16, the subject insertion body 1 is moved in the oblique direction to the position where the center axis S1 coincides with the line connecting two points P1 and P2 with the same distance from the inner face of the pipe. That is, since the line connecting the points P1 and P2 detected in advance coincides with the center axis S2 of the pipe and the center axis S1 of the subject insertion body 1 is simply oblique with respect to the center axis S2, the center axis S1 coincides with the center axis S2 by allowing the center axis S1 of the subject insertion body 1 to coincide with the line connecting the points P1 and P2. Thereafter, the subject insertion body 1 is moved in the axial direction to insert the subject insertion body 1 into the pipe. Accordingly, in the state where the center axis S1 coincides with the center axis S2, the subject insertion body 1 is inserted into the pipe.

As described above, the subject insertion body 1 is inserted into the pipe, and the pipe is thereby inspected by the inspection ultrasonic sensors 111.

The pipe processing device of the embodiment is a pipe processing device in which the subject insertion body 1 inserted from the opening portion 101h of the pipe into the pipe is provided to be movable by the movement mechanism 6 in the axial direction along the center axis S1 of the subject insertion body 1, the radial direction perpendicular to the center axis S1, the rotation direction of rotating around the center axis S1, and the oblique direction oblique with respect to the center axis S1. The pipe processing device includes the insertion end portion 2 that is provided on the front side of the subject insertion body 1 inserted into the pipe and is formed with the outer diameter smaller than inner diameter of the pipe, the axial ultrasonic sensor 21 that transmits and receives the sonic waves in the insertion direction with respect to the front end of the insertion end portion 2, the radial ultrasonic sensor 22 that transmits and receives the sonic waves in the direction intersecting the center axis S1 on the side portion of the insertion end portion 2, and the control unit 5 that controls the movement mechanism 6 according to the detection results of the axial ultrasonic sensor 21 and the radial ultrasonic sensor 22.

According to the pipe processing device, the subject insertion body 1 is disposed at a position of detecting a distance from the outer edge of the opening portion 101h of the pipe by the axial ultrasonic sensor 21; the subject insertion body 1 is moved in a radial direction to a position where the distance detected by the axial ultrasonic sensor 21 is larger than the outer edge of the opening portion 101h of the pipe; the subject insertion body 1 is moved in an axial direction to a position where the inner face of the pipe is detected by the radial ultrasonic sensor 22; a distance is detected from the inner face of the pipe by the radial ultrasonic sensor 22 while the subject insertion body 1 is rotated in a rotation direction, and the subject insertion body 1 is moved in a radial direction to a position where the distance is the same; the subject insertion body 1 is moved in an axial direction by a predetermined distance, a distance is detected from the inner face of the pipe by the radial ultrasonic sensor 22 while the subject insertion body 1 is rotated in a rotation direction, and the subject insertion body 1 is moved in a radial direction to a position where the distance is the same; and the subject insertion body 1 is moved in an oblique direction to a position where the center axis S1 matches a line connecting the two points P1 and P2 with the same distance from the inner face of the pipe, and the subject insertion body 1 is moved in an axial direction to insert the subject insertion body 1 into the pipe. For this reason, the subject insertion body 1 is inserted into the pipe with the center axis S1 matching the center axis S2 of the pipe. As a result, it is possible to guide the subject insertion body 1 for insertion so that the subject insertion body passes through the center of the pipe.

In addition, in the pipe processing device of the embodiment, the insertion end portion 2 is formed to be tapered toward the front side.

According to the pipe processing device, the subject insertion body 1 is moved in the axial direction to the position where the inner face of the pipe is detected by the radial ultrasonic sensor 22, the distance from the inner face of the pipe is detected by the radial ultrasonic sensor 22 while the subject insertion body 1 is rotated in the rotation direction, the subject insertion body 1 is moved in the radial direction to the position where the distance is the same, the subject insertion body 1 is moved in the axial direction by the predetermined distance, the distance from the inner face of the pipe is detected by the radial ultrasonic sensor 22 while the subject insertion body 1 is rotated in the rotation direction, the subject insertion body 1 is moved in the radial direction to the position where the distance is the same, and the subject insertion body 1 is moved in the oblique direction to the position where the center axis S1 matches the line connecting the two points P1 and P2 with the same distance from the inner face of the pipe. In this case, it is possible to prevent the insertion end portion 2 from coming in contact with the inner face of the pipe. As a result, it is possible to move the subject insertion body 1 to the more accurate position.

The pipe processing device of the embodiment is provided with the sensor support portion 11 that is provided on the side portion of the subject insertion body 1, in which the plurality of inspection ultrasonic sensors 111 transmitting and receiving the sonic waves in the direction intersecting the center axis S1 is disposed along the center axis S1. The plurality of sensor support portions 11 is provided at the symmetrical positions based on the center axis S1.

According to the pipe processing device, it is possible to move the inspection ultrasonic sensor 111 along the inner face of the pipe, and to inspect the pipe with high precision.

In addition, in the pipe processing device of the embodiment, the sensor support portion 11 is supported to be slidable in the radial direction perpendicular to the center axis S1, and is elastically biased in the protrusion direction.

According to the pipe processing device, since the sensor support portion 11 comes in contact with the inner face of the pipe, it is possible to move the inspection ultrasonic sensor 111 with the sensor coming in contact with the inner face of the pipe, and to inspect the pipe with high precision. In addition, since the sensor support portion 11 is moved in the radial direction along the unevenness of the inner face of the pipe, it is possible to allow the inspection ultrasonic sensor 111 to follow the shape of the inner face of the pipe, and to inspect the pipe with high precision.

In addition, in the pipe processing device of the embodiment, the sensor support portion 11 is supported to be tiltable in the front and back direction of the insertion.

According to the pipe processing device, since the sensor support portion 11 is moved in the front and back direction along the unevenness of the inner face of the pipe, it is possible to allow the inspection ultrasonic sensor 111 to follow the shape of the inner face of the pipe, and to inspect the pipe with high precision.

In addition, in the pipe processing device of the embodiment, the sensor support portion 11 supported to be tiltable in the front and back direction is elastically biased in the front direction.

According to the pipe processing device, since the front side of the subject insertion body is tapered such that the sensor support portion 11 is inclined to the front side when the subject insertion body 1 is inserted into the pipe, it is possible to smoothly perform the insertion. In the state where the subject insertion body 1 is inserted into the pipe, since the sensor support portion 11 is moved in the front and back direction along the unevenness of the inner face of the pipe, it is possible to allow the inspection ultrasonic sensor 111 to follow the shape of the inner face of the pipe, and to inspect the pipe with high precision. In addition, since the sensor support portion 11 is elastically biased in the state tilted in the front direction, it is possible to substitute the inspection ultrasonic sensor 111 as the radial ultrasonic sensor at the time of insertion when the inspection ultrasonic sensor 111 on the front side of the sensor support portion 11 is disposed at a distance from the inner face of the pipe.

In addition, in the pipe processing device of the embodiment, the sensor support portion 11 is supported to be tiltable in the circumferential direction.

According to the pipe processing device, since the sensor support portion 11 is moved in the circumferential direction along the unevenness of the inner face of the pipe, it is possible to allow the inspection ultrasonic sensor 111 to follow the shape of the inner face of the pipe, and to inspect the pipe with high precision.

In addition, in the pipe processing device of the embodiment, at least three inspection ultrasonic sensors 111 are disposed along the center axis S1 with respect to the sensor support portion 11, and the inspection ultrasonic sensor 111a positioned on the intermediate side is supported to be slidable in the protrusion direction from the outer face of the sensor support portion 11 and is elastically biased in the protrusion direction.

Since a plurality of sonic waves is transmitted and received at different angles due to arranging the plurality of inspection ultrasonic sensors 111, precision in detection is improved. When at least three inspection ultrasonic sensors 111 are disposed, the inspection ultrasonic sensor 111a on the intermediate side may be separated from the inner face of the pipe by the unevenness of the inner face of the pipe. From this point, according to the pipe processing device, since the inspection ultrasonic sensor 111a positioned on the intermediate side is elastically biased to protrude from the outer face of the sensor support portion 11, the inspection ultrasonic sensor 111a positioned on the intermediate side is prevented from being separated from the inner face of the pipe by the unevenness of the inner face of the pipe, and hence it is possible to inspect the pipe with high precision.

In addition, in the pipe processing device of the embodiment, the plurality of protrusion portions 18 provided to protrude on the side portion of the subject insertion body 1 is provided at the symmetrical positions based on the center axis S1, is supported to be slidable in the radial direction perpendicular to the center axis S1, and is elastically biased in the protrusion direction.

According to the pipe processing device, since the protrusion portion 18 is moved in the radial direction along the unevenness of the inner face of the pipe while coming in contact with the inner face of the pipe, it is possible to keep the state where the center axis S1 matches the center axis S2 of the pipe.

In addition, in the pipe processing device of the embodiment, the protrusion portions 18 are equally disposed in the circumferential direction based on the center axis S1 with the sensor support portions 11.

According to the pipe processing device, since each protrusion portion 18 and each sensor support portion 11 are equally disposed in the circumferential direction in the pipe, it is possible to stably keep the state where the center axis S1 coincides with the center axis S2 of the pipe.

In addition, in the pipe processing device of the embodiment, at least one outer corner of the subject insertion body 1, the insertion end portion 2, the sensor support portion 11, or the protrusion portion 18 is arc or chamfered-processed.

According to the pipe processing device, it is possible to smoothly move the device in a case of the insertion into the pipe, the movement in the pipe, and the extraction of the device from the pipe.

In addition, according to the embodiment, there is provided a pipe processing method for moving any one pipe processing device described above by the movement mechanism 6 to insert the pipe processing device from the opening portion 101h of the pipe into the pipe, the method including: disposing the subject insertion body 1 at a position of detecting a distance from the outer edge of the opening portion 101h of the pipe by the axial ultrasonic sensor 21; moving the subject insertion body 1 in a radial direction to a position where the distance detected by the axial ultrasonic sensor 21 is larger than the outer edge of the opening portion 101h of the pipe; moving the subject insertion body 1 in an axial direction to a position where the inner face of the pipe is detected by the radial ultrasonic sensor 22; detecting a distance from the inner face of the pipe by the radial ultrasonic sensor 22 while rotating the subject insertion body 1 in a rotation direction, and moving the subject insertion body 1 in a radial direction to a position where the distance is the same; moving the subject insertion body 1 in an axial direction by a predetermined distance, detecting a distance from the inner face of the pipe by the radial ultrasonic sensor 22 while rotating the subject insertion body 1 in a rotation direction, and moving the subject insertion body 1 in a radial direction to a position where the distance is the same; and moving the subject insertion body 1 in an oblique direction to a position where the center axis S1 matches a line connecting the two points P1 and P2 with the same distance from the inner face of the pipe, and moving the subject insertion body 1 in a rotation direction to insert the subject insertion body 1 into the pipe.

According to the pipe processing method, the subject insertion body 1 is inserted into the pipe in the state where the center axis S1 is matched with the center axis S2 of the pipe. As a result, it is possible to guide the subject insertion body 1 for insertion so that the subject insertion body 1 passes through the center of the pipe.

In addition, in the embodiment, as the pipe processing device, the pipe inspecting device provided with the inspection ultrasonic sensor 111 has been described by way of example. However, when a mechanism that performs a cutting process is provided instead of the inspection ultrasonic sensor 111, it is possible to perform the process of the pipe with high precision as the pipe processing device.

REFERENCE SIGNS LIST

1 SUBJECT INSERTION BODY INSERTION END PORTION
2a TAPERED FACE
21 AXIAL ULTRASONIC SENSOR
22 RADIAL ULTRASONIC SENSOR
3 FIXED PORTION
4 JOINT PORTION
5 CONTROL UNIT
6 MOVEMENT MECHANISM
61 AXIAL MOVEMENT PORTION
62 RADIAL MOVEMENT PORTION
63 ROTATION-DIRECTION MOVEMENT PORTION
64 OBLIQUE-DIRECTION MOVEMENT PORTION
10 MAIN BODY PORTION
11 SENSOR SUPPORT PORTION
111 (111a) INSPECTION ULTRASONIC SENSOR
12 SLIDE MOVEMENT PORTION
12a SUPPORT MEMBER
12b SLIDE PORTION
12c SLIDE SHAFT
12d COMPRESSION COIL SPRING
13 TILT MOVEMENT PORTION
13a BEARING MEMBER
13b ROTATION SHAFT
14 TILT BIASING PORTION
15 CIRCUMFERENTIAL MOVEMENT PORTION
16 SENSOR EXTRUSION PORTION
18 PROTRUSION PORTION
18a SLIDE SUPPORT PORTION
18b COMPRESSION COIL SPRING
101e MAIN WATER NOZZLE
101f MAIN WATER PIPE
101h OPENING PORTION
P1, P2 DETECTION POINT
S1 CENTER AXIS OF DEVICE
S2 CENTER AXIS OF PIPE

The invention claimed is:

1. A pipe processing device provided with an subject insertion body, which is inserted into a pipe from an opening portion of the pipe, to be movable by a movement mechanism in an axial direction along a center axis of the subject insertion body, a radial direction perpendicular to the center axis, a rotation direction of rotating about the center axis, and an oblique direction oblique with respect to the center axis, the pipe processing device comprising:
   an insertion end portion that is provided on a front side of the subject insertion body to be inserted into the pipe and is formed in a smaller outer diameter than an inner diameter of the pipe;
   an axial ultrasonic sensor that transmits and receives a sonic wave in an insertion direction with respect to a front end of the insertion end portion;
   a radial ultrasonic sensor that transmits and receives a sonic wave in a direction perpendicular to the center axis at a side portion of the insertion end portion; and
   a control unit that controls the movement mechanism according to detection results of the axial ultrasonic sensor and the radial ultrasonic sensor.

2. The pipe processing device according to claim 1, wherein the insertion end portion is formed to be tapered toward the front side.

3. The pipe processing device according to claim 1, further comprising:
   a sensor support portion that is provided on the side portion of the subject insertion body and in which a plurality of inspection ultrasonic sensors transmitting and receiving a sonic wave in a direction perpendicular to the center axis are placed in parallel to the center axis,
   wherein a plurality of the sensor support portions is provided at symmetrical positions about the center axis.

4. The pipe processing device according to claim 3, wherein the sensor support portions are supported to be slidable in a radial direction perpendicular to the center axis, and are elastically biased in a protrusion direction radially extending from the subject insertion body.

5. The pipe processing device according to claim 3, wherein the sensor support portions are supported to be tiltable in a front and back direction of insertion.

6. The pipe processing device according to claim 5, wherein the sensor support portions supported to be tiltable in the front and back direction are elastically biased in the front direction.

7. The pipe processing device according to claim 3, wherein the sensor support portions are supported to be tiltable in a circumferential direction.

8. The pipe processing device according to claim 3, wherein at least three inspection ultrasonic sensors are placed in parallel to the center axis with respect to the sensor support portions, and the inspection ultrasonic sensor positioned in a middle of a row of the inspection ultrasonic sensors is supported to be slidable in a protrusion direction radially extending from an outer face of the sensor support portion and is elastically biased in the protrusion direction.

9. The pipe processing device according to claim 3, wherein a plurality of protrusion portions provided to protrude on the side portion of the subject insertion body are provided at symmetrical positions about the center axis, are supported to be slidable in a radial direction perpendicular to the center axis, and are elastically biased in a protrusion direction.

10. The pipe processing device according to claim 9, wherein the protrusion portions are equally disposed in a circumferential direction about the center axis as a reference along with the sensor support portions.

11. The pipe processing device according to claim 9, wherein at least one outer corner of the subject insertion body, the insertion end portion, the sensor support portion, or the protrusion portion is arc or chamfered-processed.

12. A pipe processing method for moving the pipe processing device according to claim 1 by the movement mechanism to insert the pipe processing device from the opening portion of the pipe into the pipe, the method comprising:
   disposing the subject insertion body at a position of detecting a distance from an outer edge of the opening portion of the pipe by the axial ultrasonic sensor;
   moving the subject insertion body in a radial direction to a position where the distance detected by the axial ultrasonic sensor is larger than the outer edge of the opening portion of the pipe;
   moving the subject insertion body in an axial direction to a position where an inner face of the pipe is detected by the radial ultrasonic sensor;
   detecting a distance from the inner face of the pipe by the radial ultrasonic sensor while rotating the subject insertion body in a rotation direction, and moving the subject insertion body in a radial direction to a position where the distance is the same;
   moving the subject insertion body in an axial direction by a predetermined distance, detecting a distance from the inner face of the pipe by the radial ultrasonic sensor while rotating the subject insertion body in a rotation direction, and moving the subject insertion body in a radial direction to a position where the distance is the same; and
   moving the subject insertion body in an oblique direction to a position where the center axis coincides with a line connecting two points with the same distance from the inner face of the pipe and moving the subject insertion body in an axial direction to insert the subject insertion body into the pipe.

* * * * *